United States Patent

Sogabe et al.

[11] Patent Number: 5,892,103
[45] Date of Patent: Apr. 6, 1999

[54] PROCESS FOR PRODUCTION OF CARBOXYLIC ACID ESTER AND RESIN-SEPARATING VESSEL USED THEREIN

[75] Inventors: Hideki Sogabe; Takahiro Takeda, both of Himeji, Japan

[73] Assignee: Nippon Shokubai Co., Ltd., Osaka, Japan

[21] Appl. No.: 990,451

[22] Filed: Dec. 15, 1997

[30] Foreign Application Priority Data

Dec. 16, 1996 [JP] Japan ................................ 8-335592

[51] Int. Cl.$^6$ ............................ C07C 27/48; C07C 69/52
[52] U.S. Cl. ........................................ 560/218; 560/205
[58] Field of Search ........................... 560/205, 218

[56] References Cited

U.S. PATENT DOCUMENTS 3,882,167  5/1975  Lohmar et al. .......................... 560/205

FOREIGN PATENT DOCUMENTS 63-17884  1/1988  Japan .

Primary Examiner—Gary Geist
Assistant Examiner—Jafar Parsa
Attorney, Agent, or Firm—Sherman and Shalloway

[57] ABSTRACT

The present invention provides a process for producing a carboxylic acid ester by reacting a carboxylic acid with an alcohol in a suspension of a strongly acidic cation exchange resin which is a catalyst, which process comprises introducing a reaction mixture slurry containing said ion exchange resin, from a reactor for the above reaction to a resin-separating vessel, separating, in said resin-separating vessel, said reaction mixture slurry into a clear solution and a slurry-like high-concentration mixture, and discharging the clear solution from the upper section of the resin-separating vessel and the slurry-like high-concentration mixture from near the bottom of the resin-separating vessel to circulate it into the reactor. Preferably, the resin-separating vessel is operated under such conditions that the ascending speed of the clear solution becomes 0.003 m/sec or less. The process allows efficient separation/recovery of ion exchange resin from reaction mixture and reuse of recovered resin in the reaction.

4 Claims, 1 Drawing Sheet

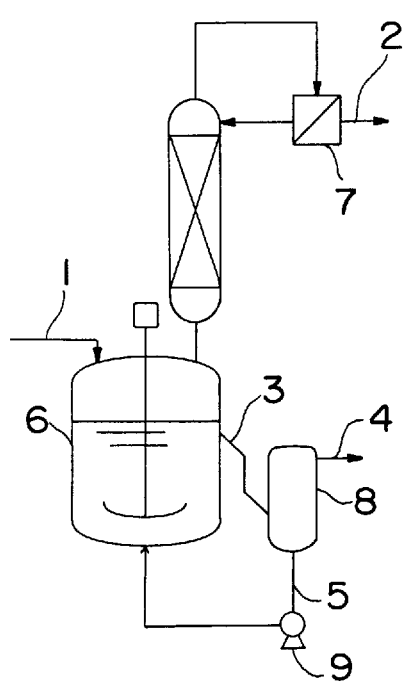
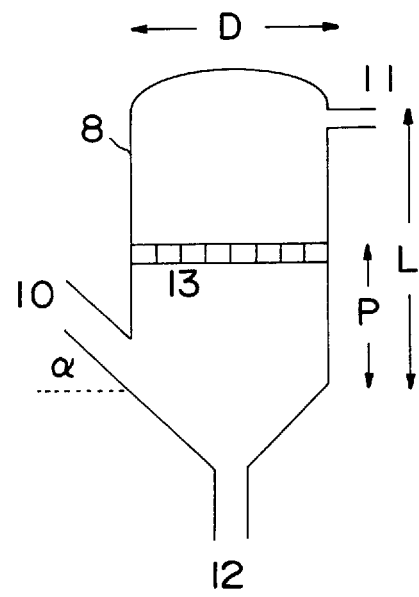
FIG. 1
FIG. 2
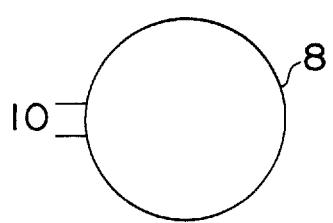
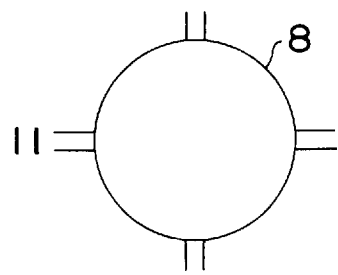
FIG. 3
FIG. 4

PROCESS FOR PRODUCTION OF CARBOXYLIC ACID ESTER AND RESIN-SEPARATING VESSEL USED THEREIN

The present invention relates to a process for producing a carboxylic acid ester and also to a resin-separating vessel used in the process. Particularly, the present invention relates to a process for producing a carboxylic acid ester by reacting a carboxylic acid with an alcohol in a suspension of a strongly acidic cation exchange resin (which is a catalyst), wherein the cation exchange resin is efficiently separated form the reaction mixture obtained and reused as a catalyst to produce a carboxylic acid ester continuously; as well as to a resin-separating vessel used in the above process.

There is known a process for producing a carboxylic acid ester continuously, which comprises reacting a carboxylic acid with an alcohol in a reactor having a strongly acidic cation exchange resin (a catalyst) fixed inside, recovering the unreacted carboxylic acid and the unreacted alcohol from the reaction mixture obtained, by distillation, and circulating the recovered carboxylic acid and alcohol for reuse. This process using a reactor having a strongly acidic cation exchange resin (a catalyst) fixed inside, however, inevitably gives a low conversion because the esterification between carboxylic acid and alcohol is an equilibrium reaction.

To alleviate the above-mentioned problem of the conventional process, Japanese Patent Application Laid-Open No. 54326/1974 proposes a process which aims at a higher conversion by introducing a gas from near the bottom of a reactor to suspend an ion exchange resin in a reaction mixture, and subjecting the reaction mixture to distillation to remove the water, ester, etc. generated by esterification, as an azeotropic mixture to shift the equilibrium to a reaction side. In this process, the ion exchange resin-containing reaction mixture is separated into the ion exchange resin and the remainder (true reaction mixture) by the use of a catalyst separator such as filter or the like.

Also, Japanese Patent Application Laid-Open No. 17884/1988 discloses a process wherein esterification is conducted while an ion exchange resin is being suspended in the system using a stirrer. In this process, an 80-mesh wire net is used for separation of ion exchange resin from reaction mixture.

Processes wherein esterification is conducted with an ion exchange resin suspended in a reaction mixture, have a merit of giving a high conversion; however, they have problems to be solved, in the means or method for separation of ion exchange resin from reaction mixture. That is, in separating an ion exchange resin by the use of a filter or a wire net as conducted in the above conventional processes, the fragments of ion exchange resin appearing during esterification or the polymers produced as by-products during esterification cause plugging of filter or wire net, making difficult the long-term operation of the apparatus used.

The conventional processes have a further problem of insufficient separation of ion exchange resin from reaction mixture. Insufficient separation leads to leakage of ion exchange resin into resin-separated reaction mixture (clear solution). When the leakage amount of ion exchange resin is large, the reaction rate is low in continuous esterification and addition of fresh ion exchange resin is necessary.

Insufficient separation of ion exchange resin from reaction mixture has a further problem. That is, in esterification of, for example, a higher alcohol, the formed ester causes hydrolysis or the like, in the step of ester purification, owing to the leaked ion exchange resin; as a result, the hydrolysis products (e.g. carboxylic acid and alcohol) remain in a final product as impurities.

Precipitation is considered as an effective method for separation of ion exchange resin from reaction mixture. This approach, however, requires a large apparatus and takes a long time for separation.

Hence, it is an object of the present invention to provide a process for producing a carboxylic acid ester by reacting a carboxylic acid with an alcohol in a suspension of a strongly acidic cation exchange resin (a catalyst), which process uses a small-sized apparatus, minimizes the leakage of ion exchange resin into clear solution, and allows efficient separation of ion exchange resin from reaction mixture over an industrially satisfactory operational period.

As a result of an extensive study, the present inventors found out that the above object can be achieved by introducing an ion exchange resin-containing reaction mixture slurry from a reactor into a resin-separating vessel, separating the slurry in the vessel into a clear solution substantially or completely free from any ion exchange resin and a slurry-like high-concentration mixture containing an ion exchange resin, and discharging the clear solution from the upper section of the resin-separating vessel and the slurry-like high-concentration mixture from near the bottom of the resin-separating vessel.

According to the present invention, there is provided a process for producing a carboxylic acid ester by reacting a carboxylic acid with an alcohol in a suspension of a strongly acidic cation exchange resin which is a catalyst, which process comprises introducing a reaction mixture slurry containing said ion exchange resin, from a reactor for the above reaction to a resin-separating vessel, separating, in said resin-separating vessel, said reaction mixture slurry into a clear solution and a slurry-like high-concentration mixture, and discharging the clear solution from the upper section of the resin-separating vessel and the slurry-like high-concentration mixture from near the bottom of the resin-separating vessel to circulate it into the reactor.

In the above process, it is preferable that the resin-separating vessel is operated under such conditions that the ascending speed of the clear solution represented by the following formula:

ascending speed V (m/sec) of clear solution=[discharging rate (m$^3$/sec) of clear solution]÷[average cross-sectional area (m$^2$) of clear solution in resin-separating vessel]

becomes 0.003 m/sec or less.

According to the present invention, there is further provided a resin-separating vessel used in the above process, which comprises:

a clear solution-discharging pipe provided at the upper section of the resin-separating vessel for discharging a clear solution out of the resin-separating vessel, a reaction mixture slurry-introducing pipe provided at the lower section of the resin-separating vessel for introducing a reaction mixture slurry from a reactor into the resin-separating vessel, and a slurry-like high-concentration mixture-discharging pipe provided near the bottom of the resin-separating vessel for discharging a slurry-like high-concentration mixture out of the resin-separating vessel, said reaction mixture slurry-introducing pipe being tilted downward relative to a horizontal line by an angle (α) of 20°–70°.

In the present invention, the "carboxylic acid" refers to a $C_{1-5}$ saturated or unsaturated carboxylic acid. As the carboxylic acid, a $C_{2-3}$ unsaturated carboxylic acid is preferred. Examples thereof are acrylic acid and methacrylic acid.

In the present invention, the "alcohol" refers to a $C_{1-12}$ saturated or unsaturated aliphatic alcohol, a $C_{3-10}$ alicyclic alcohol, or a $C_{6-10}$ aromatic alcohol. A $C_{4-12}$ aliphatic or alicyclic alcohol is preferred. Examples thereof are n-butanol, isobutanol, sec-butanol, tert-butanol, 1-pentanol, 2-pentanol, 3-pentanol, cyclopentanol, 1-hexanol, 2-hexanol, 3-hexanol, cyclohexanol, 1-heptanol, 2-heptanol, 3-heptanol, 1-octanol, isooctanol, 2-ethylhexanol, isononyl alcohol and lauryl alcohol.

Therefore, the present process is suitable for use in reaction of acrylic acid and/or methacrylic acid with a $C_{4-12}$ aliphatic or alicyclic alcohol to produce a corresponding carboxylic acid ester.

There is no particular restriction as to the strongly acidic cation exchange resin used in the present invention, and there can be used a commercial ion exchange resin known as strongly acidic cation exchange ion. Examples thereof are Amberlite IR-120B (a product of Rohm and Haas Co.), DAIAION PK-208 and PK-228 (products of Mitsubishi Chemical Corporation) and DUOLITE C-26 (a product of Sumitomo Chemical Co., Ltd.).

In the present invention, as to the operational procedure and conditions used in reaction of a carboxylic acid with an alcohol in a suspension of a strongly acidic cation exchange resin to produce a corresponding carboxylic acid ester, there is no particular restriction except for the above-mentioned matters, and the present process can be carried out according to a conventional technique.

According to the present process, the ion exchange resin-containing reaction mixture slurry after esterification is introduced into a resin-separating vessel and separated in the vessel into a clear solution and a slurry-like high-concentration mixture, and the clear solution is discharged from the upper section of the resin-separating vessel and the slurry-like high-concentration mixture is discharged from near the bottom of the resin-separating vessel.

The "clear solution" refers to a reaction mixture substantially free from the ion exchange resin, or a reaction mixture containing a significantly reduced amount of the ion exchange resin. The clear solution is composed mainly of an intended product, i.e. a carboxylic acid ester and can be purified as necessary by distillation or the like to obtain a product, i.e. a high-purity carboxylic acid ester.

The "slurry-like high-concentration mixture" refers to a slurry-like mixture obtained by removing the clear solution from the ion exchange resin-containing reaction mixture slurry, and comprises generally 10–50% by weight, preferably 20–30% by weight of the ion exchange resin and generally 90–50% by weight, preferably 80–70% by weight of the unreacted carboxylic acid, the unreacted alcohol, etc. The slurry-like high-concentration mixture is discharged from the resin-separating vessel and circulated into the reactor for reuse in esterification.

The present process is hereinafter described in detail with reference to the accompanying drawings.

BRIEF DESCRIPTION OF THE DRAWINGS

FIG. 1 is a drawing showing the process of the present invention.

FIG. 2 is a drawing showing an example of the resin-separating vessel used in the present process.

FIG. 3 is a drawing showing a state in which a reaction mixture slurry-introducing pipe is fitted to a resin-separating vessel.

FIG. 4 is a drawing showing a state in which a clear solution-discharging pipe is fitted to a resin-separating vessel.

In these drawings, 1 refers to a raw material-feeding line; 2 to a generated water-discharging line; 3 to a line for discharging of reaction mixture slurry from reactor; 4 to a clear solution-discharging line; 5 to a slurry-like high-concentration mixture-circulating line; 6 to an esterification reactor; 7 to an oil-water separator; 8 to a resin-separating vessel; 9 to a slurry pump; 10 to a reaction mixture slurry-introducing pipe; 11 to a clear solution-discharging pipe; 12 to a slurry-like high-concentration mixture-discharging pipe; and 13 to a straightening vane.

FIG. 1 shows an apparatus used in carrying out the present process. The ion exchange resin-containing reaction mixture slurry in the esterification reactor 6 is introduced into the resin-separating vessel 8 through the line 3. In the resin-separating vessel 8, the reaction mixture slurry is separated into (1) a slurry-like high-concentration mixture containing an ion exchange resin and (2) a clear solution substantially or completely free from any ion exchange resin. The clear solution is discharged through the line 4, and the slurry-like high-concentration mixture is discharged through the line 5 and circulated into the reactor 6 by the pump 9 for reuse.

The distillate discharged from the upper section of the reactor 6 is separated in the oil-water separator 7 into water and an oily matter consisting of the unreacted carboxylic acid, the formed ester, etc. The oily matter is circulated into the reactor 6 through the line 2 for reuse.

FIG. 2 is a drawing showing an example of the resin-separating vessel 8 used in the present process. The ion exchange resin-containing reaction mixture slurry discharged from the reactor 6 is introduced into the resin-separating vessel 8 from the pipe 10 through the line 3 and separated in the vessel 8 into (1) a slurry-like high-concentration mixture containing an ion exchange resin and (2) a clear solution substantially or completely free from any ion exchange resin. The clear solution is discharged from the clear solution-discharging pipe 11, and the slurry-like high-concentration mixture is discharged from the slurry-like high-concentration mixture-discharging pipe 12.

In the present process, the resin-separating vessel is preferably operated under such conditions that the ascending speed of the clear solution represented by the following formula:

ascending speed V (m/sec) of clear solution=[discharging rate (m³/sec) of clear solution]÷[average cross-sectional area (m²) of clear solution in resin-separating vessel]

becomes 0.003 m/sec or less, preferably 0.0001–0.003 m/sec. By controlling the ascending speed (i.e. the discharging rate) of the clear solution in the above range, it is possible to obtain a clear solution substantially free from any ion exchange resin, or a clear solution containing a significantly reduced amount of an ion exchange resin. When the ascending speed is higher than 0.003 m/sec, the ion exchange resin tends to leak into the clear solution. A lower ascending speed gives a clear solution of lower ion exchange resin content, but this requires use of a resin-separating vessel of larger diameter.

In carrying out the present process, it is preferable that as shown in FIG. 2, the reaction mixture slurry is introduced from the pipe 10 into the lower half of the resin-separating vessel 8 downward at an angle ($\alpha$) of 20°–70°, preferably 30°–60° relative to a horizontal line. When the reaction mixture slurry is introduced into the resin-separating vessel at an angle close to a horizontal line ($\alpha$=0), the flow in the vicinity of the slurry inlet becomes turbulent; as a result, suspension of ion exchange resin takes place, a longer time is needed for separation of reaction mixture slurry into slurry-like high-concentration mixture and clear solution, and use of a resin-separating vessel of larger capacity becomes necessary.

Preferably, the reaction mixture slurry is introduced from the pipe 10 into the resin-separating vessel 8 toward its center, as shown in FIG. 3. When the reaction mixture slurry is introduced into the resin-separating vessel 8 along a tangential direction of the vessel, the flow of the slurry in the vessel becomes an eddy, which may invite suspension of ion exchange resin.

Also preferably, a straightening vane 13 is provided in the resin-separating vessel 8 between the reaction mixture slurry-introducing pipe 10 and the clear solution-discharging pipe 11. By providing this straightening vane 13, the leakage of ion exchange resin into clear solution can be prevented effectively. There is no particular restriction as to the structure of the straightening vane 13, but a grid having meshes of about 30–200 nm is preferably used.

Also preferably, the flow rate ratio of the clear solution discharged from the clear solution-discharging pipe 11 and the slurry-like high-concentration mixture discharged from the slurry-like high-concentration mixture-discharging pipe 12 is set at clear solution/slurry-like high-concentration mixture=1/1 to 1/20, preferably 1/2 to 1/10. When the flow rate ratio is larger than 1/1, the concentration of ion exchange resin in slurry-like high-concentration mixture is too high, making difficult discharging of the slurry by pump. Meanwhile, when the flow rate ratio is smaller than 1/20, the amount of slurry-like high-concentration mixture discharged is too large; as a result, a turbulent flow is generated in the resin-separating vessel 8, suspension of ion exchange resin takes place, and the leakage of ion exchange resin into clear solution becomes large.

Also preferably, a plurality of, preferably 2–8 clear solution-discharging pipes 11 are fitted to the cross-sectional circumference of the resin-separating vessel 8 at equal intervals, as shown in FIG. 4. Thereby, the leakage of ion exchange resin into clear solution can be prevented effectively. When the discharging of clear solution is conducted only at one place, the linear speed of clear solution in the vicinity of the place becomes large, whereby the ion exchange resin may be drawn into the clear solution.

The process of the present invention can be carried out in one of various embodiments mentioned above.

The resin-separating vessel 8 used in the present process has a ratio (L/D) of the length (L) of vessel and the inside diameter (D) of vessel both shown in FIG. 2, of generally 0.8/1 to 3/1, preferably 1/1 to 2/1.

A resin-separating vessel preferable for use in the present process is a vessel wherein the above ratio (L/D) is 0.8/1 to 3/1, particularly 1/1 to 2/1 and the angle ($\alpha$) of the reaction mixture slurry-introducing pipe 10 is 20°–70°, particularly 30°–60°. A more preferable resin-separating vessel is a vessel as shown in FIG. 2 wherein the ratio (L/D) and the angle ($\alpha$) are the same as above and a straightening vane 13 is provided at such a position that the ratio (P/L) of the length (L) of vessel and the position (P) of straightening vane is 0.2 to 0.8, particularly 0.3–0.7.

The present process can be favorably carried out by using one of various preferable resin-separating vessels mentioned above.

The present invention is specifically described below by way of Examples.

EXAMPLE 1

Using, as a strongly acidic cation exchange resin, 15.5 m$^3$ (a volume in a water-wetted state) of DAIAION PK 208 (a product of Mitsubishi Chemical Corporation), esterification of acrylic acid and butanol was conducted, with stirring, in a reactor at a temperature of 80° C. under a reduced pressure of 150 mmHg. The resulting reaction mixture slurry was continuously discharged from the reactor at a rate of 112 m$^3$/hr and introduced into a resin-separating vessel 8 as shown in FIG. 2 (the vessel had no straightening vane 13). The reaction mixture slurry consisted of 21% by volume of the ion exchange resin and 79% by volume of a solution. The solution consisted of 1.99% by weight of water, 9.75% by weight of butanol, 59.59% by weight of butyl acrylate, 21.98% by weight of acrylic acid, 0.13% by weight of phenothiazine (a stabilizer) and 6.56% by weight of impurities.

The resin-separating vessel 8 had an inside diameter (D) of 1,700 mm and a length (L) of 2,000 mm. To the vessel 8 was fitted a reaction mixture slurry-introducing pipe 10 at an angle ($\alpha$) of 45° so as to face the center of the vessel 8.

A clear solution was discharged from a clear solution-discharging pipe 11 at a rate of 18 m$^3$/hr. A slurry-like high-concentration mixture (slurry concentration=25% by volume) was discharged from a slurry-like high-concentration mixture-discharging pipe 12 at a rate of 94 m$^3$/hr and circulated into the reactor. The ascending speed of the clear solution at its outlet was 0.0022 m/sec. When an operation was conducted for 10 days under the above conditions, the amount of leakage of ion exchange resin into next step was only 0.5 l.

EXAMPLE 2

Using, as a strongly acidic cation exchange resin, 10 m$^3$ of DAIAION PK 208 (a product of Mitsubishi Chemical Corporation), esterification of acrylic acid and 2-ethylhexyl alcohol was conducted, with stirring, in a reactor at a temperature of 85° C. under a reduced pressure of 70 mmHg. The resulting reaction mixture slurry was continuously discharged from the reactor at a rate of 57 m$^3$/hr and introduced into a resin-separating vessel 8 as shown in FIG. 2 (the vessel had no straightening vane 13). The reaction mixture slurry consisted of 27% by volume of the ion exchange resin and 73% by volume of a solution. The solution consisted of 0.24% by weight of water, 28.76% by weight of 2-ethylhexyl alcohol, 63.51% by weight of 2-ethylhexyl acrylate, 5.29% by weight of acrylic acid, 0.03% by weight of phenothiazine (a stabilizer) and 2.17% by weight of impurities.

The resin-separating vessel 8 had an inside diameter (D) of 1,000 mm and a length (L) of 1,500 mm. To the vessel 8 was fitted a reaction mixture slurry-introducing pipe 10 at an angle ($\alpha$) of 45° so as to face the center of the vessel 8.

A clear solution was discharged from a clear solution-discharging pipe 11 at a rate of 7 m$^3$/hr. A slurry-like high-concentration mixture (slurry concentration=31% by volume) was discharged from a slurry-like high-concentration mixture-discharging pipe 12 at a rate of 50 m$^3$/hr and circulated into the reactor. The ascending speed of the clear solution at its outlet was 0.0025 m/sec. When an operation was conducted for 10 days under the above conditions, the amount of leakage of ion exchange resin into next step was only 7 l.

EXAMPLE 3

An operation was conducted for 10 days under the same conditions as in Example 1 except that a grid-shaped straightening vane 13 was provided in the resin-separating vessel 8. The amount of leakage of ion exchange resin was 1 l. Incidentally, the position (P) of the straightening vane 13 was 1,200 m.

EXAMPLE 4

An operation was conducted for 10 days under the same conditions as in Example 1 except that there was used a resin-separating vessel having six clear solution-discharging pipes at the cross-sectional circumference of the vessel at equal intervals. The amount of leakage of ion exchange resin was 1 l.

Comparative Example 1

An operation was conducted for 10 days under the same conditions as in Example 1 except that a reaction mixture slurry was introduced into the resin-separating vessel 8 at a rate of 130 m³/hr, a clear solution was discharged from the clear solution-discharging pipe 11 at a rate of 36 m³/hr, a slurry-like high-concentration mixture was discharged from the slurry-like high-concentration mixture-discharging pipe 12 at a rate of 94 m³/hr, and the ascending speed of clear solution at its outlet was controlled at 0.0044 m/sec. As a result, the amount of leakage of ion exchange resin into clear solution was as large as 100 l.

Comparative Example 2

An operation was conducted under the same conditions as in Example 1 except that a reaction mixture slurry was introduced into the resin-separating vessel 8 at a rate of 28 m³/hr, a clear solution was discharged from the clear solution-discharging pipe 11 at a rate of 18 m³/hr, a slurry-like high-concentration mixture was discharged from the slurry-like high-concentration mixture-discharging pipe 12 at a rate of 10 m³/hr, and the ratio of the discharging rate of clear solution and the discharging rate of slurry-like high-concentration mixture was controlled at 1:0.6. As a result, the resin plugged the pump 9 used for withdrawal near from the vessel bottom and the operation was stopped. At that time, the slurry concentration in slurry-like high-concentration mixture was 59% by volume.

As is appreciated from the above Examples, the present invention can produce the following meritorious effects.

(1) Efficient separation and recovery of ion exchange resin from ion exchange resin-containing reaction mixture is possible by the use of a small-sized separator.

(2) There occurs no problem such as plugging caused by fragmentation of ion exchange resin or the like, because the separator used contains neither filter nor wire net.

(3) Since the amount of leakage of ion exchange resin into clear solution is small, decomposition of ester by ion exchange resin in ester purification step can be prevented and, moreover, the amount of ion exchange resin supplemented into reactor can be reduced.

(4) In esterification in a suspension of an ion exchange resin, the ion exchange resin used can be separated and recovered stably over a long period of time. Moreover, by circulating the recovered ion exchange resin into a reactor for reuse, esterification can be conducted continuously.

What is claimed is:

1. A process for producing a carboxylic acid ester by reacting a carboxylic acid with an alcohol in a suspension of a strongly acidic cation exchange resin which is a catalyst, which process comprises introducing a reaction mixture slurry, which comprises a first amount of a reaction mixture solution and a second amount of said ion exchange resin, from a reactor for the above reaction to a resin-separating vessel, separating, in said resin-separating vessel, said reaction mixture slurry into (i) a clear solution comprising a third amount of said reaction mixture solution and (ii) a slurry-like high-concentration mixture comprising a fourth amount of said reaction mixture solution and said second amount of said ion exchange resin, said third amount of said reaction mixture solution plus said fourth amount of said reaction mixture solution equalling said first amount of said reaction mixture solution, and discharging the clear solution from an upper section of the resin-separating vessel and the slurry-like high-concentration mixture from near the bottom of the resin-separating vessel to circulate it into the reactor.

2. The process according to claim 1, wherein the resin-separating vessel is operated under such conditions that the ascending speed of the clear solution, represented by the following formula ascending speed V (m/sec) of clear solution=(discharging rate (m³/sec) of clear solution)÷(average cross-sectional area (m²) of clear solution in resin-separating vessel)

becomes 0.003 m/sec or less.

3. A resin-separating vessel, which comprises:

a vertical vessel body having a top and a bottom, at least one clear solution-discharging pipe provided at an upper section of the vessel body, for discharging a clear solution out of the vessel body, a reaction mixture slurry-introducing pipe provided at a lower section of the vessel body, for introducing a reaction mixture slurry into the vessel body, a slurry-like high-concentration mixture discharging pipe provided near the bottom of the vessel body, for discharging a slurry-like high-concentration mixture out of the vessel body, said reaction mixture slurry-introducing being tilted downward to a horizontal line by an angle of 20°–70°.

4. The resin separating vessel according to claim 3, wherein said at least one clear solution-discharging pipe comprises a plurality of clear solution-discharging pipes fitted to a cross-sectional circumference of the vessel body at equal intervals.

* * * * *